United States Patent [19]

Lam et al.

[11] Patent Number: 5,760,063
[45] Date of Patent: Jun. 2, 1998

[54] ARYLHYDRAZONE DERIVATIVES USEFUL AS ANTIBACTERIAL AGENTS

[75] Inventors: Kelvin T. Lam, Belmont; David G. Powers, Maynard, both of Mass.

[73] Assignee: Scriptgen Pharmaceuticals, Inc., Medford, Mass.

[21] Appl. No.: 713,724

[22] Filed: Sep. 13, 1996

Related U.S. Application Data

[60] Provisional application No. 60/003,787 Sep. 15, 1995.
[51] Int. Cl.$^6$ ................................ A01N 37/34
[52] U.S. Cl. ................ 514/355; 514/443; 514/523; 514/639; 546/286; 546/287; 546/288; 546/289; 546/290; 546/291; 546/292; 546/293; 546/296; 546/297; 546/329; 546/330; 546/332; 549/57; 552/8
[58] Field of Search .................... 514/639, 523, 514/355, 357, 443; 546/639, 286, 287, 288, 289, 291, 292, 293, 296, 297, 329, 330, 332; 549/57; 552/8; 558/394, 412, 415, 416, 418, 419, 422; 564/149, 155, 164, 251

[56] References Cited

U.S. PATENT DOCUMENTS

| | | | |
|---|---|---|---|
| 2,658,889 | 11/1953 | Goldberg et al. | 260/193 |
| 3,157,569 | 11/1964 | Addor et al. | 167/30 |
| 3,839,564 | 10/1974 | Wright et al. | 514/523 |
| 4,830,957 | 5/1989 | Sato et al. | 430/562 |
| 4,837,142 | 6/1989 | Sato et al. | 430/562 |

FOREIGN PATENT DOCUMENTS

| | | | |
|---|---|---|---|
| 765569 | 11/1979 | France | 514/639 |
| 1355304 | 6/1974 | United Kingdom . | |

OTHER PUBLICATIONS

Hassaneen et al., *Heterocycles*, 36(8):1775–1781, 1993.

*Primary Examiner*—James H. Reamer
*Attorney, Agent, or Firm*—Darby & Darby

[57] ABSTRACT

The subject invention, provides arylhydrazone compounds having the Formula 1:

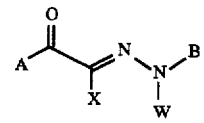

wherein A and B are independently aryl or heteroaryl and A and B independently are substituted with at least one group selected from alkyl, halogen, CN, COOR$^7$, NR$^7$R$^8$, CONR$^7$R$^8$, NO$_2$, SR$^7$, SOR$^7$, SO$_2$R$^7$, NHCOR$^7$, NHSO$_2$R$^7$, OR$^7$, hydroxyalkyl, and aminoalkyl. The compounds of this invention are useful for treating a wide variety of bacterial infections, including diseases of the skin, e.g., acne and skin ulcers, gastroenteritis, colitis, meningitis, keratinitis, conjunctivitis, diseases of the urinary and genital tracts, etc.

19 Claims, No Drawings

ARYLHYDRAZONE DERIVATIVES USEFUL AS ANTIBACTERIAL AGENTS

This is a continuation of Provisional application No. 60/005,787, filed Sep. 15, 1995.

FIELD OF THE INVENTION

The present invention relates to novel arylhydrazone derivatives, their preparation, to pharmaceutical compositions containing them, and to methods of using them to alleviate bacterial infections.

BACKGROUND OF THE INVENTION

New classes of antibacterial agents are needed to address both the growing resistance of bacteria to present therapies and the general lack of efficacy of existing antibiotics against slow-growing organisms. Although bacterial infections were once considered well controlled, the threat posed by the emergence of multidrug-resistant organisms is now well accepted. Desirable characteristics for new antibacterial products include activity against drug resistant organisms, reduced propensity for resistance development, greater biological half-life in humans, reduced liability for allergic reactions, and broad spectrum antibacterial activity.

U.S. Pat. No. 2,658,889 discloses compounds having Formula 1:

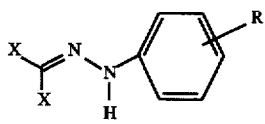

wherein each X is cyano and R is lower alkoxy, lower alkenoxy, and lower carboxylic acid acylamido. The disclosed utility of these compounds is as anthelmintics.

U.S. Pat. No. 3,157,569 describes compounds having the Formula 2

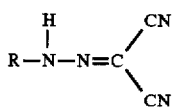

wherein R is a phenyl or a naphthyl group. These groups can be substituted with halo, dihalo, alkyl or alkoxy substituents. These compounds are useful as pesticides.

South African patent 68/5645 discloses compounds of the Formula 3:

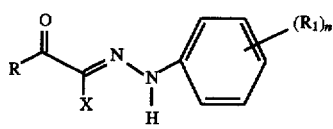

where each $R_1$ is alkyl, alkoxy, or an electronegative group and n is 1–5; X is halogen, cyano, nitro, or azido; and R is alkyl, alkoxy, dialkylamino or alkyl(aryl)amino. The compounds were reported as having utility as insecticides and acaricides. German patent 2 128 008 discloses similar compounds and demonstrates bactericidal utility against phytopathogens (specifically *Xanthomonas oryzae*, responsible for "bacterial leaf blight of rice").

GB Patent 1,355,304, and DE patent 2 222 147 disclose compounds having Formula 4:

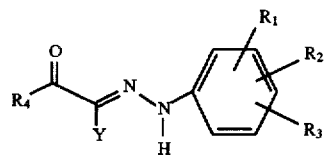

where Y is cyano and at least one of $R_{1-3}$ is a substituent other than hydrogen. The other two of $R_{1-3}$ substituents can be a halo, alkyl, alkoxy, cyano, nitro, trifluoromethyl, phenylazo, or p-chlorophenyl group. The $R_4$ group is phenyl, naphthyl, furyl, thienyl, or phenyl substituted with halogen, alkyl, or alkoxy. The compounds demonstrated utility as insecticides.

U.S. Pat. No. 4,837,142 discloses compounds having Formula 5:

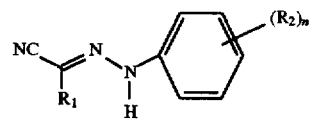

wherein $R_1$ can be $-COR_{11}$ wherein $R_{11}$ can be an aryl or a heterocyclic group and $R_2$ includes halo, cyano carboxyl, carbonyl, and sulfonyl groups. These compounds are disclosed as dyes which are coupled to a light sensitive group. The dye-coupled compounds are useful in color photographic processes. The following applications and patents U.S. Pat. No. 4,830,957; JP 61-270757; GB 1,426,689; JP 49-118723; DE 2 413 223; JP 58-65758; JP 22-35058; GB 1,341,132 DE-2 413 189; and DE 2 516 968 disclose compounds similar to those discussed above which are also used for preparing photographic dyes.

SUMMARY OF THE INVENTION

The present invention, provides arylhydrazone compounds having the Formula I:
wherein A and B are independently aryl or heteroaryl and A and B independently are substituted with at least one group selected from alkyl, halogen, CN, $COOR^7$, $NR^7R^8$, $CONR^7R^8$, $NO_2$, $SR^7$, $SOR^7$, $SO_2R^7$, $NHCOR^7$, $NHSO_2R^7$, $OR^7$, hydroxyalkyl, and aminoalkyl.

$R^7$ and $R^8$ are independently hydrogen, alkyl, alkenyl, and haloalkyl.

W is hydrogen, alkyl, alkanoyl, or cycloalkanoyl;

X is CN, $CONR^7R^8$, $NO_2$, $SO_2R^7$, $N_3$, or halogen.

Further, the invention includes salts of the compounds of Formula I.

Additionally provided are pharmaceutical compositions comprising a compound of Formula I or a salt thereof and a pharmaceutically acceptable carrier. Further contemplated by the present invention are dosage unit forms that include these compositions. Also contemplated is a method of using a compound of Formula I for treatment of bacterial infections in a mammal. The method comprises administering a compound of Formula I or a salt thereof to a mammal in need of the treatment.

DETAILED DESCRIPTION OF THE INVENTION

The antibacterial activity of the compounds of this invention makes them useful for treatment of a wide variety of bacterial infections. Compounds of this invention have been shown to inhibit transcription of DNA into RNA in an in vitro system and in bacteria. This inhibition, which is believed to be responsible for the compounds' antibacterial effects, is lethal to bacteria and the infection is eliminated from the host.

The aryl and heteroaryl groups useful in practicing the subject invention are groups having from 6 to about 10 carbon atoms and one or two rings. Preferably the aryl and heteroaryl groups will have from 1 to about 6 carbon atoms. These groups include substitution at all positions such as, for example, 2-, 3-, and 4-pyridyl. Examples of suitable aryl and heteroaryl groups include but are not limited to groups, such as, for example, phenyl, naphthyl, pyridyl, pyrazinyl, indolyl, indolinyl, benzofuryl, biphenyl, bipyridyl, phenylpyridyl, pyridylphenyl, benzothienyl, quinolyl, isoquinoyl, and the like.

Examples of the preferred aryl and heteroaryl groups are phenyl, naphthyl, indolyl, indolinyl, benzofuryl, benzothienyl, biphenyl, bipyridyl, phenylpyridyl, and pyridylphenyl.

The alkyl and alkenyl groups useful in practicing the subject invention are straight, branched, or cyclic groups. These groups can have from 1 to about 18 carbon atoms. Preferably the alkyl and alkenyl groups will have from 1 to about 8 carbon atoms. Most preferably the alkyl and alkenyl groups will have from 1 to about 6 carbon atoms. Non-limiting examples of the alkyl and alkenyl groups include methyl, ethyl, propyl, isopropyl, butyl, isobutyl, tert-butyl, allyl, and the like.

The cycloalkyl and cycloalkenyl groups can have from 3 to about 15 carbon atoms and one or two rings. Preferably the cycloalkyl and cycloalkenyl rings will have from 3 to about 8 carbon atoms. Examples of the cycloalkyl and cycloalkenyl groups include cyclopentyl, cyclopentenyl, cyclohexyl, cyclohexenyl, and the like.

The haloalkyl groups can have from 1 to about 4 carbon atoms and at have at least one halogen atom selected from the group consisting of fluorine, chlorine or bromine. These include groups with a single type of halogen atom or mixtures of halogen atoms and include perhalo groups. Non-limiting examples of the haloalkyl groups include groups such as, for example, chloromethyl, chloroethyl, dichloromethyl, dichloroethyl, trichloromethyl, fluoromethyl, fluoroethyl, difluoromethyl, difluoroethyl, trifluoromethyl, bromomethyl, bromoethyl, and the like.

The compounds of the invention include pharmaceutically acceptable salts of alkali metals, alkaline earth metals, and pharmaceutically acceptable acid addition salts. Examples of metals which are useful in forming salts include metals such as, for example, sodium, potassium, calcium, magnesium, and the like. Preferred pharmaceutically acceptable acid addition salts include but are not limited to acids such as, for example, hydrochloric, sulfuric, maleic, succinic, citric, methanesulfonic and toluenesulfonic, and the like.

Aryl hydrazones of the type shown in Formula (1) are generally prepared by the condensation of an aryldiazonium salt, prepared from an aniline in the presence of a mineral acid and an alkali-metal nitrite, with a compound containing a methylene unit that is substituted with two electron withdrawing functional groups, such as, for example acyl, benzoyl, substituted benzoyl, cyano, sulfonyl, alkoxycarbonyl, nitro, halo, azido, carboxamide, and the like.

The preferred electron withdrawing groups are acyl, benzoyl, substituted benzoyl, cyano, and methyl sulfonyl.

The preparation of compounds of the Formula I use solvents, such as, for example, water, and water miscible organic solvents such as ethanol, methanol, acetic acid and the like. The organic solvents typically are used to solubilize the active methylene compound. The reaction is preferably carried out in the pH range of from about 4 to about 8. Optionally, bases such as sodium acetate, sodium carbonate, sodium hydroxide or a mixture of any of the foregoing, can be used for buffering of the solution of the active methylene compound. The reaction temperatures are generally from about 20° C. to about +30° C., preferably from about −10° C. to about +10° C. Typically, the starting materials are used in equimolar portions. The reactions are generally complete within about an hour. However, extended reaction times may be required. The arylhydrazones are usually solids that precipitate from the reaction mixture and are isolable by filtration. The materials obtained are generally very pure.

Analytically pure samples may be obtained by recrystallization from an appropriate solvent. Preferred solvents for recrystallization include methanol, ethanol, and acetic acid and the like.

Utilities

The ability of the disclosed compounds to inhibit *E.coli* RNAP S and inhibit bacterial growth indicates that they are useful for treating a wide variety of bacterial infections in mammals, including diseases of the skin, e.g., endocarditis, acne and skin ulcers, gastroenteritis, colitis, meningitis, keratinitis, conjunctivitis, diseases of the urinary and genital tracts, e.g., syphillis and ghonorrhea, breast disease (mastitis), osteomyelitis, otitis, as well as diseases of the lungs, e.g. pneumonia and tuberculosis. The compounds are generally active in treating diseases caused by *Staphyllococcus aureus*. In addition, the compounds are valuable for sterilizing the gut in the course of surgery.

Dosage Forms

The antibacterial agents of this invention can be administered by any means that produces contact of the active agent with the agents' site of action in the body of a mammal. They can be administered by any conventional means available for use in conjunction with pharmaceuticals, either as individual therapeutic agents or in a combination of therapeutic agents. This is meant to include internal as well as topical administration. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. Usually, a daily dosage of active ingredient can be from about 5 to about 50 milligrams per kilogram of body weight. Ordinarily, when the compounds of this invention are used, the daily dosage will range from about 5 to about 50, milligrams per kilogram per day.

This may be administered in 1 to 4 oral doses or in sustained release form, effective to obtain the desired results. These drugs may also be administered parenterally. The dosages may be increased when treating severe or life-threatening infections.

Dosage forms (compositions) suitable for internal administration contain from about 100 milligrams to about 1 gram of active ingredient per unit.

In these pharmaceutical compositions, the active ingredient will ordinarily be present in an amount of about 0.5 to about 95%, by weight, based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

The dosage forms can include powdered carriers, such as lactose, sucrose, mannitol, starch, cellulose derivatives, magnesium stearate, stearic acid, and the like. Further, tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to enhance patient acceptance.

In general, water, a suitable oil, saline, aqueous dextrose (glucose), and related sugar solutions and glycols such as propylene glycol or polyethylene glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances.

Antioxidants such as, for example, sodium bisulfate, sodium sulfite, citric acid and its salts, sodium EDTA, ascorbic acid, and the like can be used either alone or in combination with other suitable antioxidants or stabilizing agents typically employed in the pharmaceutical compositions. In addition, parenteral solutions can contain preservatives, such as, for example, benzalkonium chloride, methyl- or propyl-paraben, chlorobutanol and the like.

Dosage unit forms can also include any of excipients; diluents; disintegrants; lubricants; plasticizers; colorants; and dosing vehicles. Suitable pharmaceutical carriers are described in *Remington's Pharmaceutical Sciences*, A. Osol, a standard reference text in this field.

EXAMPLES

The following examples will serve to illustrate the invention but are not meant to be limiting. The precursor compounds used in these reactions are prepared by methods known in the art.

Example 1

Method A

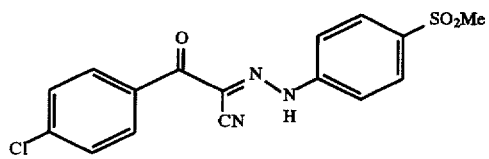

In a round bottom flask equipped with a stirbar is placed 4-(methyl-sulfonyl)-aniline (427.5 mg, 2.5 mmol) in 100 mL of $H_2O$. To this suspension is added concentrated HCl (1.0 mL) and the reaction cooled to 0° C. To the cooled solution is added $NaNO_2$ (175 mg, 2.5 mmol) in 10 mL of $H_2O$ and the mixture stirred at 0° C. for 30 minutes. In another round bottom flask equipped with a stirbar is placed 4-chlorobenzoylacetonitrile (447.5 mg, 2.5 mmol) and sodium acetate (1000 mg) in 100 mL of $H_2O$. The solution of the diazonium salt of the aniline is then added dropwise with stirring to the solution containing the α-cyanoketone, stirring is continued for an hour. The precipitated product is isolated by vacuum filtration and recrystallized from ethanol to afford yellow needles.

M.P.=259°–260° C.

M.S. (EI)=362 [M+H]$^+$.

Example 2

Method B

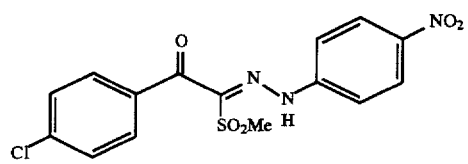

In a round bottom flask equipped with a stirbar is placed 4-nitroaniline (127.5 mg, 1.0 mmol) in 1 0 mL of $H_2O$. To this suspension is added concentrated $H_2SO_4$ (0.4 mL) and acetic acid (2.0 mL) and the reaction is cooled to 0° C. To the cooled solution is added $NaNO_2$ (69 mg, 1.0 mmol) in 2 mL of $H_2O$ and the mixture stirred at 0° C. for 30 minutes. In another round bottom flask equipped with a stirbar is placed 4-chlorobenzoylmethylsulfone (233 mg, 1.0 mmol) and sodium acetate (10 g) in 200 mL of 1:1 methanol/$H_2O$. The solution of the diazonium salt of the aniline is then added dropwise with stirring to the solution containing the b-ketosulfone; stirring is continued for an hour. The precipitated product is isolated by vacuum filtration and recrystallized from ethanol to afford yellow needles.

M.P.=209°–211 ° C.

Example 3

Method C

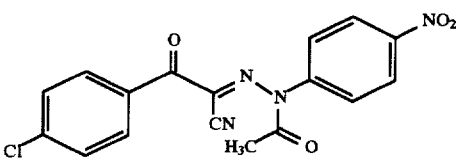

In a round bottom flask equipped with a stirbar is placed 2-(4-nitrophenyl)hydrazono-3-oxo-3-(4-chlorophenyl) propionitrile (380 mg, 1.16 mmol) in 7 mL of acetic anhydride. This stirred suspension is heated at reflux until the reaction becomes homogenous. The reaction is then allowed to cool to room temperature. The precipitated product is isolated by vacuum filtration to afford pale yellow needles.

M.P.=254°–256° C.

M.S. (EI)=371 [M+H]$^+$.

Examples 4–14

Compounds were prepared following the procedures outlined in Examples 1–3. These were based on Formula II, below. The formulas and physical data are given in Table 1.

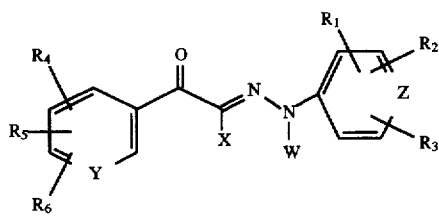

Formula II (II) in vivo Assays

S. aureus cells were grown up in a shake culture overnight at 37° C. in LB medium. This culture was diluted to an O.D. of 0.1 with the following medium: 0.3% peptone, 0.2% $MgSO_4 7H_2O$, 0.05% $CaCl_2 2H_2O$, and 0.05% yeast extract. The culture was divided into a series of parallel cultures and returned to the shaker at 37° C. After thirty minutes, the radioactive precursors were added: [methyl-$H^3$]thymidine, [5,6-$H^3$]uracil, or N-acetyl-D-[1- $H^3$]glucosamine purchased from Amersham, at 1 µCi/mL. After twenty minutes, a sample was collected out of the culture and treated with an

TABLE 1

| Ex. | R¹ | R² | R³ | R⁴ | R⁵ | R⁶ | W | X | Y | Z | Method A, B, C | M.P. |
|---|---|---|---|---|---|---|---|---|---|---|---|---|
| 4. | 4-SMe | H | H | 4-Cl | H | H | H | CN | CH | CH | A | 178–79° C. |
| 5. | 4-SOMe | H | H | 4-Cl | H | H | H | CN | CH | CH | A | 158–59° C. |
| 6. | 4-NO₂ | H | H | 4-C₆H₅ | H | H | H | CN | CH | CH | B | 283–85° C. |
| 7. | 4-NHSO₂Me | H | H | 4-Cl | H | H | H | CN | CH | CH | B | 210–11° C. |
| 8. | 4-NO₂ | H | H | 4-Cl | H | H | H | CN | N | CH | B | 250–52° C. |
| 9. | 4-CO₂H | H | H | 4-Cl | H | H | H | CN | CH | CH | B | 266–67° C. |
| 10. | 4-NHCOMe | H | H | 4-Cl | H | H | H | CN | CH | CH | B | 221–23° C. |
| 11. | 4-SO₂Me | H | H | 4-C₆H₅ | H | H | H | CN | CH | CH | B | 263–64° C. |
| 12. | H | H | H | 4-Cl | H | H | H | CN | CH | N | B | 171–72° C. |
| 13. | 4-Cl | H | H | 4-C₆H₅ | H | H | H | CN | CH | CH | B | 228–29° C. |
| 14. | 4-Cl | H | H | 4-Cl | H | H | COMe | CN | CH | CH | C | — |

As can be seen in Table 2 below, compounds of Formula I exert both an in vitro effect on a bacterial transcription system, and in vivo an antibacterial effect. A description of the biological assays follows.

(I) High Throughput in vitro Transcription (RNAP) Assay

The reagents are added to the DMSO/compound with a Tomtec Quadra. The Quadra acts as 96-tip pipetman, combined with a movable base. The reagents and compounds are stored and used in 96-well polypropylene u-bottom microtiter plates.

The Quadra is run in backfill mode (filled with water). A total of 45 mL of reagents must be added. This is divided into a 20 ml RNAP/Txn Buffer mix and a 25 ml DNA/NTP/water mix. The RNAP mix is added first to allow the drug a chance to interact with RNAP before RNAP interacts with DNA (this interaction lasts less than 5 seconds). The mixing of the reagents is done with a multivortexer after all reagents have been added (setting 5.5 for 90 seconds).

After incubation for 60 minutes, the reaction is stopped with 150 ml 10% TCA, which also precipitates the RNA. The RNA is allowed to sit a room temperature for approximately 15–45 minutes (until all plates have been stopped and the cell harvester has been set up).

The TCA precipitated RNA is transferred to double-thick glass filtermats using a Tomtec cell harvester. The wells of the microtiter plate are washed with 5% TCA and sucked through the same filtermat. Two additional washes with 5 % TCA solution are sufficient to reduce background counts.

The filters are then dried at 60° for 60 minutes. It is important to remove all of the liquid, or this may quench the scintillation fluid when it is added.

The dry filters are sealed into plastic bags with a heat-sealer. A hole is cut in one corner and 12 ml of "β-plate scintillant" is added to each bag.

It is important to use a scintillation fluid that does not cause the radiolabelled RNA and the ink from the filtermat to bleed. When choosing a scintillation counting program on the Wallac Microb 1450, it is important to choose one which counts using the appropriate window for $P^{32}$. Each well is counted for 3 seconds. The data obtained is used to calculate an $IC_{50}$ value.

equal volume of 15% TCA. Another treatment of radioactivity followed for the remainder of the culture, at 1 µCi/mL. This collection and precipitation of sample, followed by treatment with radioactivity for the remaining culture, was repeated every twenty minutes over three hours. Antibiotics and controls (i.e. rifampicin and DMSO) were added at the second timepoint. The samples were collected and precipitated on a 96 well microtiter plate. At the end of three hours, the samples containing the radioactive glucosamine were placed on ice for thirty minutes then placed in a 90° C. water bath for twenty minutes. The reactions were then captured on a Wallac printed filtermat B utilizing a Tomtec Harvester 96. The filters were dried and radioactivity was determined by a Wallac 1450 Microbeta liquid scintillation counter.

(III) MIC Assay

Compounds were prepared to a concentration of 10 mM in 100% DMSO. These were then diluted to 200 µM with 50 mM tris. A 2% DMSO solution was prepared in 50 mM tris as well as a 20 µM solution of rifampicin in 2% DMSO with 50 mM tris. With each compound and control, one to one dilutions were made in a serial dilution fashion across microtiter plates with 50 mM tris. The highest concentration was 200 µM for each compound and 20 µM for rifampicin. The lowest concentrations were 1.562 µM and 0.156 µM for the compounds and rifampicin respectively.

S. aureus, E. coli, Psuedomonas aeruginosa, Enterobacter cloacae, and Enterococcus faecium cells had been grown up in a shake culture overnight at 37° C. in LB medium. These were diluted 500 fold and added to the compounds at an equal volume. The highest compound concentration was now 100 µM, and 10 µM for rifampicin. Baseline O.D. readings were taken at 595 nm utilizing a Bio-Rad 3550-UV plate reader. A second reading was taken after 18 hours.

Example 15

The compounds of the invention were tested for antibacterial activity as described above. The results are given in Table 2.

TABLE 2

| | | E. Coli RNAP S. IC50 | Aur. MIC | PS* | CL* | FAE* |
|---|---|---|---|---|---|---|
| Ex. 15 | (structure) | +++ | + | + | +++ | ++ |
| Ex. 16 | (structure) | ++ | + | + | ++ | + |

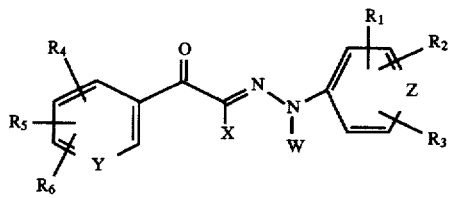

Formula II

| Ex. | $R^1$ | $R^2$ | $R^3$ | $R^4$ | $R^5$ | $R^6$ | W | X | Y | Z | E. coli RNAP IC50 | S.Aur MIC | PS* | CL* | FAE* |
|---|---|---|---|---|---|---|---|---|---|---|---|---|---|---|---|
| 1. | 4-SO$_2$Me | H | H | 4-Cl | H | H | H | CN | CH | CH | +++ | + | + | +++ | + |
| 2. | 4-NO$_2$ | H | H | 4-Cl | H | H | H | SO$_2$Me | CH | CH | ++ | NT | + | ++ | + |
| 3. | 4-NO$_2$ | H | H | 4-Cl | H | H | COMe | CN | CH | CH | ++ | + | + | ++ | + |
| 4. | 4-SMe | H | H | 4-Cl | H | H | H | CN | CH | CH | ++ | + | + | ++ | + |
| 5. | 4-SOMe | H | H | 4-Cl | H | H | H | CN | CH | CH | ++ | + | + | ++ | + |
| 6. | 4-NO$_2$ | H | H | 4-C$_6$H$_5$ | H | H | H | CN | CH | CH | ++ | + | + | ++ | 1 |
| 7. | 4-NHSO$_2$Me | H | H | 4-Cl | H | H | H | CN | CH | CH | ++ | NT | + | ++ | + |
| 8. | 4-NO$_2$ | H | H | 4-Cl | H | H | H | CN | N | CH | ++ | NT | NT | NT | NT |
| 9. | 4-CO$_2$H | H | H | 4-Cl | H | H | H | CN | CH | CH | + | NT | + | + | + |
| 10. | 4-NHCOMe | H | H | 4-Cl | H | H | H | CN | CH | CH | + | NT | + | + | + |
| 11. | 4-SO$_2$Me | H | H | 4-C$_6$H$_5$ | H | H | H | CN | CH | CH | + | NT | + | + | + |
| 12. | H | H | H | 4-Cl | H | H | H | CN | CH | N | + | + | + | ++ | + |
| 13. | 4-Cl | H | H | 4-C$_6$H$_5$ | H | H | H | CN | CH | CH | + | + | + | + | + |
| 14. | 4-Cl | H | H | 4-Cl | H | H | COMe | CN | CH | CH | + | + | + | ++ | + |
| 17. | 4-NO$_2$ | H | H | 4-Cl | H | H | H | CN | CH | CH | +++ | ++ | + | +++ | +++ |
| 18. | 4-OCF$_2$ | H | H | 4-Cl | H | H | H | CN | CH | CH | ++ | ++ | + | ++ | ++ |
| 19. | 4-Cl | H | H | 4-Cl | H | H | H | CN | CH | CH | ++ | + | + | ++ | + |
| 20. | 3-CF$_2$ | 3-CF$_2$ | H | H | H | H | H | CN | CH | CH | ++ | ++ | + | ++ | + |
| 21. | 4-F | H | H | 4-OCF$_3$ | H | H | H | CN | CH | CH | ++ | ++ | + | ++ | + |
| 22. | 4-NO$_2$ | H | H | 3-Cl | H | H | H | CN | CH | CH | + | NT | + | + | + |
| 23. | 4-NO$_2$ | H | H | H | H | H | H | CN | CH | CH | + | ++ | + | ++ | + |
| 24. | 4-NO$_2$ | Cl | Cl | Cl | H | H | H | CN | CH | CH | + | ++ | + | + | + |

+ (>10 μM), ++ (0.5–10 μM), +++ (<0.5 μM), NT = not tested.
*PS = *Psuedomonas aeruginosa*
CL = *Enterobacter cloacae*
FAE = *Enterococcus faecium*

All patents, patent applications, and literature references cited in this application are incorporated by reference in their entirety.

The invention has been described above by reference to preferred embodiments but, as those skilled in the art will

What is claimed is:

1. A compound having Formula I:

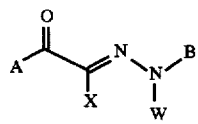

I wherein A and B are independently phenyl, naphthyl, pyridyl, pyrazinyl, indolyl, indolinyl, benzofuryl, biphenyl, bipyridyl, phenylpyridyl, pyridylphenyl, benzothienyl, quinolyl or isoquinolyl; and A and B independently are substituted with at least one group selected from alkyl, halogen, CN, $COOR^7$, $NR^7R^8$, $CONR^7R^8$, $NO_2$, $SR^7$, $SOR^7$, $SO_2R^7$, $NHCOR^7$, $NHSO_2R^7$, $OR^7$, hydroxyalkyl, and aminoalkyl;

$R^7$ and $R^8$ are independent hydrogen, alkyl, alkenyl, or haloalkyl;

W is hydrogen, alkyl, alkanoyl, or cycloalkanoyl;

X is CN or $SO_2R^7$; pharmaceutically acceptable salts thereof; and wherein when X is CN, W is H, A is phenyl or phenyl substituted by alkyl, halogen, $OR^7$, or A is naphthyl, furyl or thienyl, then B is not phenyl, or phenyl substituted by alkyl, halogen, $OR^7$, CN or $NO_2$.

2. The compound of claim 1 wherein A is 4-chlorophenyl and B is 4-nitrophenyl or 4-($SO_2Me$)phenyl.

3. The compound of claim 1 wherein X is CN or $SO_2Me$.

4. The compound of claim 1 wherein A is 3-chlorophenyl or 4-trifluoromethoxyphenyl and B is 3-trifluoromethylphenyl.

5. The compound of claim 1 wherein B is 4-fluorophenyl.

6. The compound of claim 1 wherein A is a substituted pyridyl or phenyl.

7. The compound of claim 1 wherein B is a substituted pyridyl or phenyl.

8. A pharmaceutical composition comprising a compound according to claim 1 and a pharmaceutically acceptable carrier or diluent.

9. A method of treating bacterial infections in a mammal wherein an effective amount of the compound of claim 1 is administered to a mammal in need of said treatment.

10. The method of claim 9 wherein the compound is administered topically.

11. The method of claim 9 wherein the compound is administered orally.

12. The method of claim 9 wherein the compound is administered parenterally.

13. A method for treating infections caused by *Staphylococcus aureus* in a mammal wherein an effective amount of the compound having Formula I:

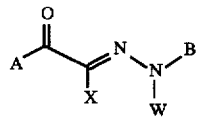

I wherein A and B are independently phenyl, naphthyl, pyridyl, pyrazinyl, indolyl, indolinyl, benzofuryl, biphenyl, bipyridyl, phenylpyridyl, pyridylphenyl, benzothienyl, quinolyl or isoquinolyl; and A and B independently are substituted with at least one group selected from alkyl, halogen, CN, $COOR^7$, $NR^7R^8$, $CONR^7R^8$, $NO_2$, $SR^7$, $SOR^7$, $SO_2R^7$, $NHCOR^7$, $NHSO_2R^7$, $OR^7$, hydroxyalkyl, and aminoalkyl;

$R^7$ and $R^8$ are independent hydrogen, alkyl, alkenyl, or haloalkyl;

W is hydrogen, alkyl, alkanoyl, or cycloalkanoyl;

X is CN, $CONR^7R^8$, or $SO_2R^7$; and pharmaceutically acceptable salts thereof; is administered to the mammal in need of said treatment.

14. A method for treating dermatologic infections in a mammal wherein an effective amount of the compound of claim 1 is administered to the mammal in need of said treatment.

15. The method of claim 14 wherein the infection is endocarditis, skin ulcers or acne.

16. A method of treating urinary and genital tract infections in a mammal wherein an effective amount of the compound of claim 1 is administered to a mammal in need of said treatment.

17. The method of claim 16 wherein the infection is syphillis, ghonorrhea, gastroenteritis, duodenal ulcer or colitis.

18. A method of treating tuberculosis in a mammal wherein an effective amount of the compound of claim 1 is administered to the mammal in need of said treatment.

19. A method of gut sterilization in surgery performed on a mammal wherein an effective amount of the compound of claim 1 is applied to the gut during surgery.

* * * * *